(12) United States Patent
McCormack et al.

(10) Patent No.: US 6,309,736 B1
(45) Date of Patent: *Oct. 30, 2001

(54) LOW GAUGE FILMS AND FILM/ NONWOVEN LAMINATES

(75) Inventors: Ann Louise McCormack, Cumming; Kevin George Hetzler, Alpharetta; Karen Lynn English, Marketta; Billy Ray Jones, Jr., Cumming; Charles John Morell, Roswell; Wiliam Bela Haffner, Kennesaw; Glynis Allicia Walton, Roswell, all of GA (US); Lance James Garrett, Jr., Neenah, WI (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/882,712

(22) Filed: Jun. 25, 1997

Related U.S. Application Data (63) Continuation-in-part of application No. 08/724,435, filed on Oct. 1, 1996, now Pat. No. 6,075,179, which is a continuation of application No. 08/359,986, filed on Dec. 20, 1994, now abandoned.

(51) Int. Cl.[7] .................................................. A61F 13/15
(52) U.S. Cl. ................... 428/198; 428/315.5; 428/316.6; 442/370; 442/394; 442/398
(58) Field of Search .................................. 428/316.6, 336, 428/315.5, 198; 442/370, 394, 398

(56) References Cited

U.S. PATENT DOCUMENTS

| 2,527,299 | 10/1950 | De Phillips | 154/50 |
| 3,276,944 | 10/1966 | Levy | 161/150 |

(List continued on next page.)

FOREIGN PATENT DOCUMENTS

| 803714 | 1/1969 | (CA) . |
| 3724510 A1 | 2/1989 | (DE) . |

(List continued on next page.)

OTHER PUBLICATIONS

Japanese Abstract 03–198724A
Japanese Abstract 02–162–008A

(List continued on next page.)

Primary Examiner—Elizabeth M. Cole (57) ABSTRACT

Disclosed herein is a low gauge, multilayer film which may be laminated to other materials such as, for example, fibrous nonwoven webs. The multilayer film may include one or more skin layers which in certain configurations comprise no more than about 15 percent of the overall thickness and in other configurations no more than about 10 percent of the overall thickness of the multilayer film. Such films and laminates have a wide variety of uses including, but not limited to, personal care absorbent products, articles of clothing and health care related items such as surgical drapes and gowns.

32 Claims, 2 Drawing Sheets

| | | | | | | | |
|---|---|---|---|---|---|---|---|
| 3,338,992 | 8/1967 | Kinney | 264/24 | 5,110,670 | 5/1992 | Janocha et al. | 428/216 |
| 3,341,394 | 9/1967 | Kinney | 161/72 | 5,110,677 | 5/1992 | Barmore et al. | 428/349 |
| 3,502,538 | 3/1970 | Petersen | 161/150 | 5,116,662 | 5/1992 | Morman | 428/198 |
| 3,502,763 | 3/1970 | Hartmann | 264/210 | 5,143,679 | 9/1992 | Weber et al. | 264/288.8 |
| 3,510,344 | 5/1970 | Dunderdale | 117/76 | 5,164,258 | 11/1992 | Shida et al. | 428/319.3 |
| 3,676,242 | 7/1972 | Prentice | 156/62.4 | 5,167,652 | 12/1992 | Mueller | 604/385.1 |
| 3,692,618 | 9/1972 | Dorschner et al. | 161/72 | 5,169,712 | 12/1992 | Tapp | 428/315.5 |
| 3,802,817 | 4/1974 | Matsuki et al. | 425/66 | 5,176,953 | 1/1993 | Jacoby et al. | 428/315.5 |
| 3,836,423 | 9/1974 | Wagner et al. | 161/159 | 5,204,429 | 4/1993 | Kaminsky et al. | 526/308 |
| 3,849,241 | 11/1974 | Butin et al. | 161/169 | 5,236,963 | 8/1993 | Jacoby et al. | 521/92 |
| 3,973,063 | 8/1976 | Clayton | 428/35 | 5,244,716 | 9/1993 | Thornton et al. | 428/198 |
| 4,041,203 | 8/1977 | Brock et al. | 428/157 | 5,261,899 | 11/1993 | Visscher et al. | 604/367 |
| 4,087,486 | 5/1978 | Fielding et al. | 260/897 | 5,272,236 | 12/1993 | Lai et al. | 526/348.5 |
| 4,104,404 | 8/1978 | Bieler et al. | 428/35 | 5,277,970 | 1/1994 | Schuhmann et al. | 428/323 |
| 4,178,401 | 12/1979 | Weinberg et al. | 428/35 | 5,278,272 | 1/1994 | Lai et al. | 526/348.5 |
| 4,185,135 | 1/1980 | Huff | 428/96 | 5,300,365 | 4/1994 | Ogale | 428/461 |
| 4,196,240 | 4/1980 | Lustig et al. | 428/35 | 5,317,035 | 5/1994 | Jacoby et al. | 521/143 |
| 4,239,826 | 12/1980 | Knott, II et al. | 428/35 | 5,340,646 | 8/1994 | Morita et al. | 428/307.3 |
| 4,254,175 | 3/1981 | Kubat et al. | 428/213 | 5,453,318 | 9/1995 | Giacobbe | 428/286 |
| 4,275,119 | 6/1981 | Weiner | 428/516 | 5,472,775 | 12/1995 | Objeski et al. | 428/220 |
| 4,294,889 | 10/1981 | Hashimoto | 428/515 | 5,539,124 | 7/1996 | Etherton et al. | 548/402 |
| 4,296,156 | 10/1981 | Lustig et al. | 428/35 | 5,554,775 | 9/1996 | Krishnamurti et al. | 556/7 |
| 4,332,845 | 6/1982 | Nawata et al. | 428/35 | 5,695,868 | 12/1997 | McCormack | 428/283 |
| 4,339,495 | 7/1982 | Weiner | 428/349 | 6,075,179 | 6/2000 | McCormack et al. | |
| 4,340,641 | 7/1982 | Weiner | 428/349 | | | | |
| 4,344,999 | 8/1982 | Gohlke | 428/212 | | | | |
| 4,353,945 | 10/1982 | Sampson | 428/90 | | | | |
| 4,384,024 | 5/1983 | Mitchell et al. | 428/349 | | | | |
| 4,399,173 | 8/1983 | Anthony et al. | 428/35 | | | | |
| 4,433,026 | 2/1984 | Molde | 428/252 | | | | |
| 4,434,258 | 2/1984 | Schumacher et al. | 524/13 | | | | |
| 4,494,629 | 1/1985 | Raeburn | 188/65.5 | | | | |
| 4,501,797 | 2/1985 | Super et al. | 428/349 | | | | |
| 4,522,203 | 6/1985 | Mays | 128/132 | | | | |
| 4,533,509 | 8/1985 | Gust et al. | 264/171 | | | | |
| 4,533,602 | 8/1985 | Nakamura et al. | 428/447 | | | | |
| 4,552,714 | 11/1985 | Krueger et al. | 264/171 | | | | |
| 4,560,598 | 12/1985 | Cowan | 428/35 | | | | |
| 4,595,629 | 6/1986 | Mays | 428/286 | | | | |
| 4,606,970 | 8/1986 | Sharps, Jr. | 428/301 | | | | |
| 4,613,643 | 9/1986 | Nakamura et al. | 524/426 | | | | |
| 4,615,922 | 10/1986 | Newsome et al. | 428/35 | | | | |
| 4,636,424 | 1/1987 | Amemiya et al. | 428/198 | | | | |
| 4,698,372 | 10/1987 | Moss | 521/145 | | | | |
| 4,702,954 | 10/1987 | Duncan | 428/213 | | | | |
| 4,725,481 | 2/1988 | Ostapchenko | 428/213 | | | | |
| 4,761,324 | 8/1988 | Rautenberg et al. | 428/198 | | | | |
| 4,777,073 | 10/1988 | Sheth | 428/155 | | | | |
| 4,816,328 | 3/1989 | Saville et al. | 428/246 | | | | |
| 4,829,096 | 5/1989 | Kitamura et al. | 521/79 | | | | |
| 4,833,026 | 5/1989 | Kausch | 428/315.5 | | | | |
| 4,842,741 | 6/1989 | Coughlin et al. | 210/500.36 | | | | |
| 4,863,792 | 9/1989 | Mrozinski | 428/315.5 | | | | |
| 4,921,653 | 5/1990 | Aoyama et al. | 264/41 | | | | |
| 4,923,650 | 5/1990 | Antoon, Jr. et al. | 264/41 | | | | |
| 4,929,303 | 5/1990 | Sheth | 156/209 | | | | |
| 4,935,287 | 6/1990 | Johnson et al. | 428/198 | | | | |
| 4,980,227 | 12/1990 | Sekiguchi et al. | 428/241 | | | | |
| 5,008,296 | 4/1991 | Antoon, Jr. et al. | 521/91 | | | | |
| 5,011,698 | 4/1991 | Antoon, Jr. et al. | 426/395 | | | | |
| 5,032,450 | 7/1991 | Rechlicz et al. | 428/196 | | | | |
| 5,055,338 | 10/1991 | Sheth et al. | 428/155 | | | | |

FOREIGN PATENT DOCUMENTS

| | | |
|---|---|---|
| 0061238 | 9/1982 | (EP) . |
| 0221726 | 5/1987 | (EP) . |
| 0247897 | 12/1987 | (EP) . |
| 0259128 | 3/1988 | (EP) . |
| 0265544 | 5/1988 | (EP) . |
| 0347019 | 8/1989 | (EP) . |
| 0347745 | 12/1989 | (EP) . |
| 0395204 | 10/1990 | (EP) . |
| 0434115 | 6/1991 | (EP) . |
| 0505027 | 9/1992 | (EP) . |
| 1453649 | * 10/1976 | (GB) . |
| 1452424 | 10/1976 | (GB) . |
| 1557920 | 12/1979 | (GB) . |
| 2223446 | 4/1990 | (GB) . |
| 2267459 A | 12/1993 | (GB) . |
| 4-227260 | 8/1992 | (JP) . |
| 95/27005 | 10/1995 | (WO) . |
| 96/19346A | 6/1996 | (WO) . |
| 98/02609A | 1/1998 | (WO) . |
| 98/02610A | 1/1998 | (WO) . |

OTHER PUBLICATIONS

Abstract of JP 01–079249.
Abstract of JP 01–146733.
Abstract of JP 05–230251.
Abstract of JP 01–271240.
Abstract of JP 54–038344.
Abstract of JP 50–076187.
NRL Report 4364 "Manufacture of Superfine Organic Fibers" by V.A. Wente, E.L. Boone and C.D. Fluharty.
NRL Reproprt 5265 "An Improved Device for the Formation of Superfine, Thermoplastic Fibers" by K.D. Lawrence, R.T. Lukas and J.A. Young.

* cited by examiner

LOW GAUGE FILMS AND FILM/NONWOVEN LAMINATES

RELATED APPLICATIONS

This is a continuation-in-part application of U.S. patent application Ser. No. 08/724,435, filed Oct. 1, 1996, now U.S. Pat. No. 6,075,179, which is itself a continuation of U.S. application Ser. No. 08/359,986 filed Dec. 20, 1994 now abandonded. The entire contents of the aforesaid application are incorporated herein by reference.

FIELD OF INVENTION

The present invention is directed to low gauge, multilayer films with skin layers that are extremely thin. In addition, the present invention is directed to such films laminated to other materials such as, for example, fibrous nonwoven webs.

BACKGROUND OF THE INVENTION

The present invention is directed to extremely thin multilayer films and their use with laminates. Such materials have a wide variety of uses, especially in the areas of limited use and disposable items.

Many products today require highly engineered components and yet, at the same time, these products are required to be limited use or disposable items. By limited use or disposable, it is meant that the product and/or component is used only a small number of times or possibly only once before being discarded. Examples of such products include, but are not limited to, surgical and health care related products such as surgical drapes and gowns, disposable work wear such as coveralls and lab coats and a personal care absorbent products such as diapers, training pants, incontinence garments, sanitary napkins, bandages, wipes and the like. All of these products can and do utilize as components, films and fibrous nonwoven webs. While both materials are often used interchangeably, films tend to have greater barrier properties, especially to liquids, while fibrous nonwoven webs have, among other things, better tactile, comfort and aesthetic properties. When these materials are used in limited use and/or disposable products, the impetus for maximizing engineered properties while reducing cost is extremely high. To this end, it is often desirable to use either a film or a nonwoven to achieve the desired results because the combination often becomes more expensive. In the area of films, there have been previous attempts to make multilayer films with reduced thicknesses. See, for example, U.S. Pat. No. 5,261,899 to Vischer wherein a three layer film is made with a central layer that comprises from about 30 to 70% of the total thickness of the multilayer film. One advantage in forming multilayer films is that specific properties can be designed into the film, and, by making the films multilayer the more costly ingredients can be relegated to the outer layers where they are most likely to be needed.

In addition, in the production of a breathable filled film it is common to employ a significant percent (by weight) of filler such as, for example, $CaCO_3$. As is known in the art, stretching of the filled film creates a fine pore network which allows the film to continue to act as a barrier to liquids and particulate matter yet allow air and water vapor to pass therethrough. In order to obtain more uniform barrier and vapor transmission properties throughout the film it is desirable to have the filler equally distributed throughout the film. Thus, although such breathable barriers may act as a barrier to liquids and particulate matter they may themselves be a source of unwanted particles (i.e. the filler). This may be undesirable in various applications or articles employing the barrier fabric. A filled film which retains good breathability while having reduced particle fallout is therefore desirable. In this regard, there exists a continuing need for a multilayer film having outer layers with little or no filler, yet which does not significantly reduce the breathability of the multilayer film. Moreover, many filled films fail to provide good adhesion to additional layers, such as, for example, nonwoven fabrics. Multilayer films which are capable of providing good adhesion to a support fabric without loss of breathability is likewise needed.

It is therefore an object of the present invention to provide a multilayer film which can be engineered to overcome problems experienced by those skilled in the art and provide specific properties while having a very thin gauge. Another object of the present invention is to combine low gauge films with other support layers such as layers of fibrous nonwoven webs to improve processing, to increase strength, and to provide aesthetic properties. A further object of the present invention is to provide a multilayer filled film having good breathability while having improved thermal adhesion and/or reduced particle fallout. The means by which such objectives are achieved can be more fully comprehended by a review of the following specification, drawings and claims.

SUMMARY OF THE INVENTION

The present invention is directed to multilayer films and multilayer film/nonwoven laminates. The films are made by conventional film forming techniques such as cast and blown coextrusion film forming processes. The films are created with a core layer made from an extrudable thermoplastic polymer with the core layer defining a first exterior surface and a second exterior surface. In the most basic configuration, a first skin layer is attached, usually simultaneously by the coextrusion process, to the first exterior surface of the core layer to form a multilayer film. The multilayer film defines an overall thickness with the first skin layer defining a first skin thickness which comprises less than about 10 percent of the overall thickness of the multilayer film. This is due to the stretching of the extruded film to such a degree so as to thin the multilayer film to within the dimensions defined herein. As a result, the thickness of the first skin layer will not exceed about 2 microns. Given the extremely thin nature of the multilayer film, it may be desirable to laminate the multilayer film to another material such as a support layer. Suitable support layers include, but are not limited to, such materials as other films, fibrous nonwoven webs, woven materials, scrims, netting and combinations of the foregoing. In other embodiments of the present invention, the core layer may have a first skin layer attached to the first exterior surface of the core layer and a second skin layer attached to the second exterior surface of the core layer. In such situations the first skin and the second skin layer should have a combined thickness which does not exceed about 15 percent of the overall thickness and more desirably where neither the first skin thickness nor the second skin thickness exceeds more than about 7.5 percent of the overall thickness of the multilayer film. If desired, one or more of the layers may contain other additives such as, for example, a particulate filler. Most typically, such fillers will be primarily utilized in the core layer in, for example, a weight percent of at least about 40 percent, based upon the total weight of that particular layer, more preferably about 40% to about 70% by weight.

It is also possible to make multilayer films which are breathable either through the use of specialized polymers which permit diffusion of gases through the layers and/or through the use of particulate fillers. Normally, to make such films breathable, they are stretched and/or crushed between compression rollers so as to create voids in and around the particles to permit the transmission of water vapor and other gases. Typically such breathable multilayer films will have water vapor transmission rates of at least 300 grams per square meter per 24 hours (g/m$^2$/day).

Such films and laminates have a wide variety of uses including, but not limited to, applications in personal care absorbent articles including diapers, training pants, sanitary napkins, incontinence devices, bandages and the like. These same films and laminates also may be used in items such as surgical drapes and gowns as well as various articles of clothing either as the entire article or simply as a component thereof.

DETAILED DESCRIPTION OF THE INVENTION

Figure 1:
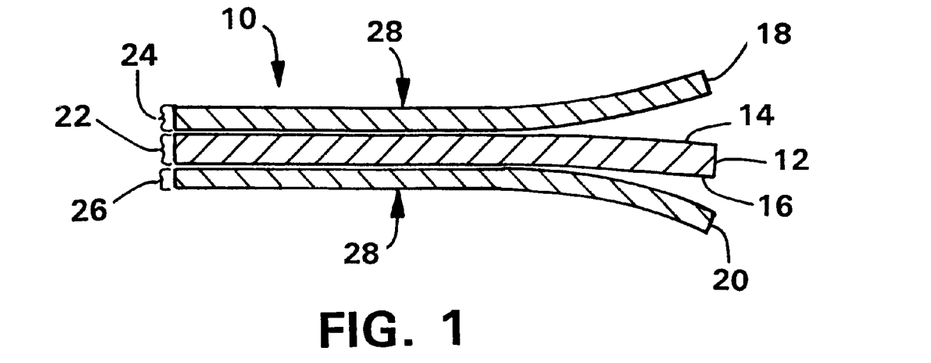
FIG. 1 is a cross-sectional side view of a multilayer film according to the present invention. The right side of the film has been split apart to facilitate its description.

The present invention is directed to multilayer films, that is, films having two or more layers as well as such films laminated to support layers such as, for example, fibrous nonwoven webs. Referring to FIG. 1, there is shown, not to scale, a multilayer film 10 which, for purposes of illustration, has been split apart at the right side of the drawing. The multilayer film 10 includes a core layer 12 made from an extrudable thermoplastic polymer such as a polyolefin, including copolymers and/or blends thereof. The core layer 12 has a first exterior surface 14 and a second exterior surface 16. The core layer also has a core thickness 22. Attached to the first exterior surface 14 of the core layer 12 is a first skin layer 18 which has a first skin thickness 24. Attached to the second exterior surface 16 of the core layer 12 is an optional second skin layer 20 which has a second skin thickness 26. In addition, the multilayer film 10 has an overall thickness 28. Such multilayer films 10 can be formed by a wide variety of processes well known to those of ordinary skill in the film forming industry. Two particularly advantageous processes are cast film coextrusion processes and blown film coextrusion processes. In such processes, the two or three layers are formed simultaneously and exit the extruder in a multilayer form. Due to the extremely thin nature of the multilayer films according to the present invention such processes will most likely prove to be the most advantageous though it also may be possible to form multilayer films using separate extrusion processes. For more information regarding such processes, see, for example, U.S. Pat. Nos. 4,522,203; 4,494,629 and 4,734,324 which are incorporated herein by reference in their entirety.

An important feature of the present invention is the ability to utilize a more generic core layer 12 in conjunction with a much thinner and more specially designed skin layer such as the first skin layer 18 or a combination of two or more skin layers attached to either or both sides of the core layer 12. Thus, it is possible to form multilayer films 10 with many layers of material. The core layer 12 as with the first skin layer 18 and optional second skin layer 20 may be formed from any polymers which are capable of being utilized in multilayer film constructions including, but not limited to, polyolefins including homopolymers, copolymers, and/or blends. To further reduce the cost of the core layer 12 one or more types of fillers may be added to the core layer polymer extrusion blend. Both organic and inorganic fillers may be used. The fillers should be selected so as to not chemically interfere with or adversely affect the extruded film. These fillers can be used to reduce the amount of polymer being used for the core layer 12 and/or to impart particular properties such as breathability and/or odor reduction. Examples of fillers can include, but are not limited to, calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivatives, polymer particles, chitin and chitin derivatives.

The amount of filler that can be used resides within the discretion of the end-user, however, additions of from 0 to 80% by weight based upon the total weight of the core layer 12 are possible. Generally the fillers will be in particulate form and usually will have somewhat of an irregular shape with average particle sizes in the range of about 0.1 to about 7 microns. The term "particle size" as used herein refers to the longest single dimension of the particle. Furthermore, if sufficient filler is used in combination with sufficient stretching of the multilayer film 10, then voids can be created around the particles contained within the core layer 12 thereby making the core layer breathable. Loadings of about 40 to about 70 percent by weight of the core layer 12 when combined with stretching provides films which have good breathability. Such breathable films will generally have Water Vapor Transmission Rates (WVTR) in excess of 300 grams per square meter per 24 hours (g/m$^2$/day) and more desirably WVTRs in excess of 800 g/m$^2$/day; 2000 g/m$^2$/day; 3000 g/m$^2$/day, and even 4000 g/m$^2$/day.

The skin layers 18 and 20 will typically include extrudable thermoplastic polymers and/or additives which provide specialized properties to the multilayer film 10. Thus, the first skin layer 18 and/or the second skin layer 20 may be made from polymers which give such properties as antimicrobial activity, water vapor transmission, adhesion and/or antiblocking properties. Thus, the particular polymer or polymers chosen for the skin layer 18 and 20 will depend upon the particular attributes desired. Examples of possible polymers that may be used alone or in combination include homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU) and olefinic thermoplastic elastomers which are multistep reactor products wherein an amorphous ethylene propylene random copolymer is molecularly dispersed in a predominately semicrystalline high polypropylene monomer/low ethylene monomer continuous matrix.

In applications where good breathability (i.e. high WVTR) is desired, the skin layers preferably comprise, at least in part, an extrudable water vapor transmissive polymer; examples include, but are not limited to, ethylene-vinyl acetate, ethylene-methyl acrylate, polystyrene, polyurethane, polyamide and mixtures thereof. The EVA and EMA copolymers preferably contain no more than about 80% ethylene by weight of the copolymer. Desirably the skin layer(s) comprise from about 30% to 100% water vapor transmissive polymer and from 0 to about 70% by weight a polyolefin based polymer, and even more desirably the vapor transmissive polymer can comprise from about 40% to about 60% by weight of the skin layer. Additionally, the skin layer may comprise two or more water vapor transmissive polymers such as, for example, 30% to 70% by weight EVA or EMA with 30% to 70% by weight polystyrene.

In addition, it may be desirable to add an anti-block material to improve processing and/or prevent unwanted adhesion of a tacky skin layer to other surfaces; as an example, some skin layers will adhere to the multilayer film itself when wound on a roll. Thus, it will often be desirable to add from 0 to about 10% anti-block material to the skin layers, and even more desirable from about 0.5 to about 5% by weight. Particulate matter such as diatamaceous earth can be added to the skin layers, although other anti-block materials may be used including, but not limited to, ground silica. Desirably the anti-block particles comprise particles having a median particle size of about 6–10 microns.

Figure 2:
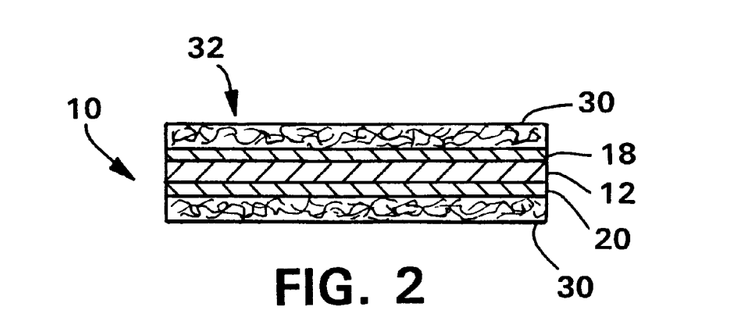
FIG. 2 is a cross-sectional side view of a multilayer film/nonwoven laminate according to the present invention.

Oftentimes it may be desirable to laminate the multilayer film 10 to one or more substrates or support layers 30 such as is shown in FIG. 2. The core layer may not have sufficient adhesive or attachment properties so as to make it bondable to the support layer 30. As a result, the first skin layer 18 may comprise a polymer or polymers which exhibit higher adhesive properties and/or a lower tack point than the core layer 12.

A desired result with respect to the material of the present invention is to achieve a very low overall film thickness and more importantly, skin layers which are only a small percentage of the overall thickness of the multilayer film 10. As demonstrated by the examples below, based upon the overall thickness 28 of the multilayer film 10, in two layer constructions the first skin thickness 24 of the first skin layer 18 should not exceed more than 10 percent of the overall thickness 28. In three layer film constructions the combined thickness of the first skin layer 18 and second skin layer 20 should not exceed 15 percent of the overall thickness and generally, the first skin layer 18 should not exceed more than 7.5 percent and even more desirably each skin layer does not exceed over 5 percent of the overall film thickness 28. The same is also true with respect to the second skin layer 20. In a further aspect, the skin layer or layers each have an individual thickness 24, 26 less than about 2 microns, desirably less than about 1.0 microns and still more desirably less than about 0.5 microns. As a result, the core thickness 22 comprises at least 85 percent of the overall thickness 28 and the first skin layer 18 and second skin layer 20 each generally will comprise no more than 7.5 percent of the overall thickness 28. Generally, it has been possible to create thinned films with overall thicknesses, about 30 microns or less and in certain applications with skin layers that do not exceed two microns. Desirably, the overall thickness 28 is less than about 25 microns and even more desirably less than about 20 microns. This is made possible by first forming a multilayer film 10 and then stretching or orienting the film in the machine direction, as explained in greater detail below, such that the resultant multilayer film 10 has increased strength properties in the machine direction or "MD", i.e., the direction which is parallel to the direction of the film as it is taken off the film extrusion equipment.

The resultant film can, if desired, be laminated to one or more support layers 30 as are shown in FIG. 2. The support layers 30 as shown in FIG. 2 are fibrous nonwoven webs. The manufacture of such fibrous nonwoven webs is well known to those of ordinary skill in the art of nonwoven manufacturing. Such fibrous nonwoven webs can add additional properties to the multilayer film 10 such as, a more soft, cloth-like feel. This is particularly advantageous when the multilayer film 10 is being used as a barrier layer to liquids in such applications as outer covers for personal care absorbent articles and as barrier materials for hospital, surgical, and clean room applications such as, for example, surgical drapes, gowns and other forms of apparel.

Attachment of the support layers 30 to the first skin layer 18 and second skin layer 20 may be by the use of a separate adhesive such as hot-melt and solvent based adhesives or through the use of heat and/or pressure as with heated bonding rolls. As a result, it may be desirable to design either or both the first skin layer 18 and the second skin layer 20 so as to have inherent adhesive properties to facilitate the lamination process.

A particularly advantageous support layer is a fibrous nonwoven web. Such webs may be formed from a number of processes including, but not limited to, spunbonding, meltblowing, hydroentangling, air-laid and bonded carded web processes. Meltblown fibers are formed by extruding molten thermoplastic material through a plurality of fine, usually circular, die capillaries as molten threads or filaments into a high velocity usually heated gas stream such as air, which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described in various patents and publications, including NRL Report 4364, "Manufacture of Super-Fine Organic Fibers" by B. A. Wendt, E. L. Boone and C. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676,242, issued Jul. 11, 1972, to Prentice; and U.S. Pat. No. 3,849,241, issued Nov. 19, 1974, to Buntin, et al. The foregoing references are incorporated herein by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbond nonwoven webs is illustrated in patents such as Appel et al., U.S. Pat. No. 4,340,563; Matsuki, et al, U.S. Pat. No. 3,802,817; Dorschner et al., U.S. Pat. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; U.S. Pat. No. 5,382,400 to Pike et al.; and Harmon, Canadian Patent Number 803,714. All of the foregoing references are incorporated herein by reference in their entirety. A 10 to 70 grams per square meter (gsm) spunbond web such as, for example, polypropylene fibers, is an exemplary support fabric.

Multilayer support layers 30 also may be used. Examples of such materials can include, for example, spunbond/meltblown laminates and spunbond/meltblown/spunbond laminates such as are taught in Brock et al., U.S. Pat. No. 4,041,203 which is incorporated herein by reference in its entirety.

Bonded carded webs are made from staple fibers which are usually purchased in bales. The bales are placed in a picker which separates the fibers. Next the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern though the web can be bonded across its entire surface if so desired. When using bicomponent staple fibers, through-air bonding equipment is, for many applications, especially advantageous.

Figure 3:
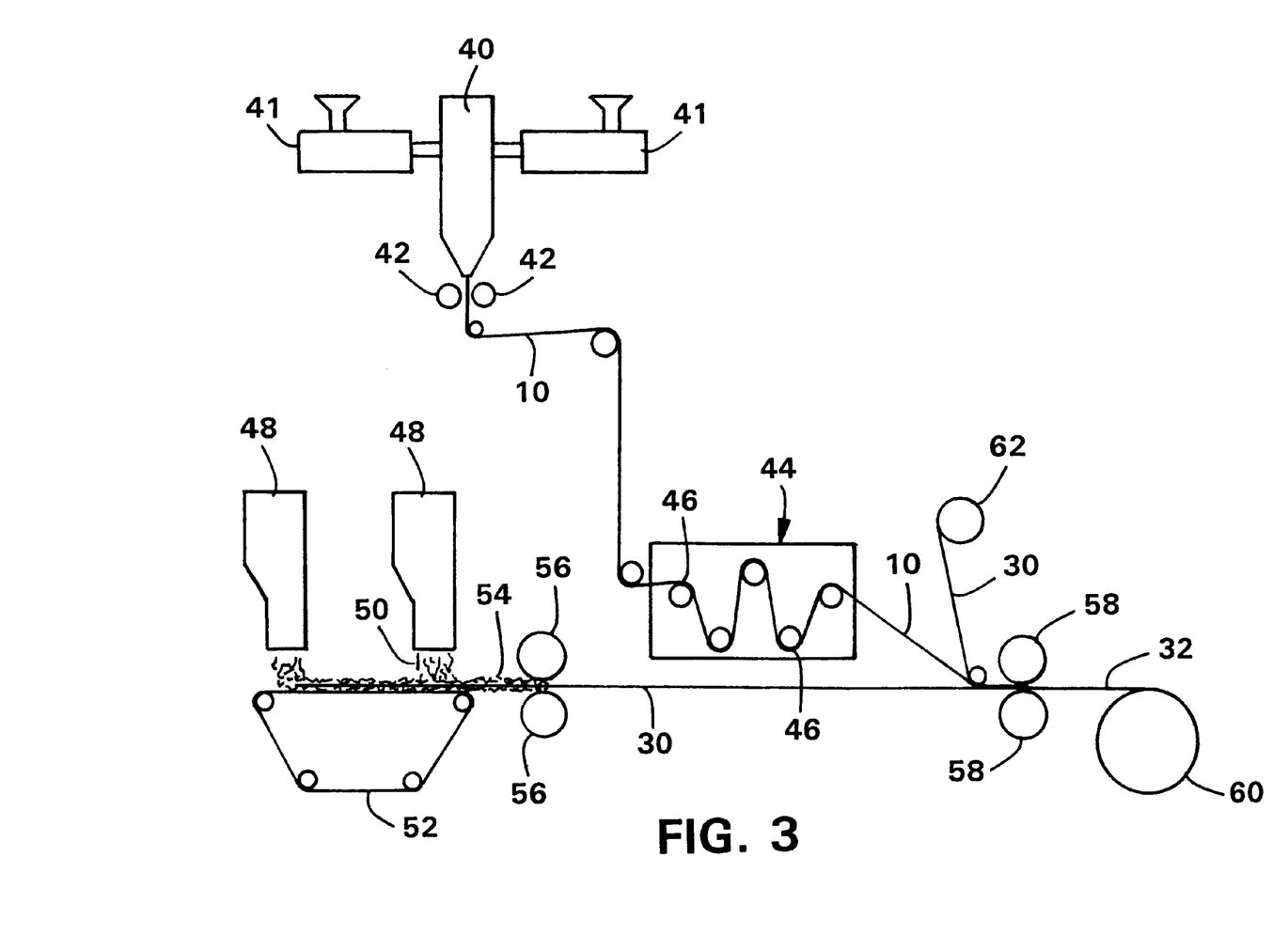
FIG. 3 is a schematic side view of a process for forming a multilayer film according to the present invention and a multilayer film/nonwoven laminate according to the present invention.

A process for forming the multilayer film 10 is shown in FIG. 3 of the drawings. Referring to the figure, the multilayer film 10 is formed from a coextrusion film apparatus 40 such as a cast or blown unit as was previously described above. Typically the apparatus 40 will include two or more polymer extruders 41. The multilayer film 10 is extruded into a pair of nip or chill rollers 42 one of which may be patterned so as to impart an embossed pattern to the newly formed film 10. This is particularly advantageous to reduce the gloss of the film and give it a matte finish. Using a three layer film construction such as is shown in FIG. 1, typically the multilayer film 10, as initially formed, will have an overall thickness 28 of approximately 40 microns or greater with the first skin layer 18 and the second skin layer 20 each having initial thicknesses of 3 microns or greater which collectively is approximately 15% of the overall initial thickness.

From the coextrusion film apparatus 40 the film 10 is directed to a film stretching unit 44 such as a machine direction orienter or "MDO" which is a commercially available device from vendors such as the Marshall and Williams Company of Providence, Rhode Island. Such an apparatus 44 has a plurality of stretching rollers 46 which progressively stretch and thin the multilayer film 10 in the machine direction of the film which is the direction of travel of the film 10 through the process as shown in FIG. 3. After exiting the film stretching unit 44 the film 10 should have a maximum thickness of approximately 30 microns and each of the skin layers should have a maximum thickness of no more than about 2 microns which in turn is collectively less than about 15 percent of the overall film and more desirably less than 10 percent of the overall film thickness.

If desired, the multilayer film 10 may be attached to one or more support layers 30 to form a multilayer film/nonwoven laminate 32. Referring again to FIG. 3, a conventional fibrous nonwoven web forming apparatus 48, such as a pair of spunbond machines, is used to form the support layer 30. The long, essentially continuous fibers 50 are deposited onto a forming wire 52 as an unbonded web 54 and the unbonded web 54 is then sent through a pair of bonding rolls 56 to bond the fibers together and increase the tear strength of the resultant web support layer 30. One or both of the rolls are often heated to aid in bonding. Typically, one of the rolls 56 is also patterned so as to impart a discrete bond pattern with a prescribed bond surface area to the web 30. The other roll is usually a smooth anvil roll but this roll also may be patterned if so desired. Once the multilayer film 10 has been sufficiently thinned and oriented and the support layer 30 has been formed, the two layers are brought together and laminated to one another using a pair laminating rolls or other means 58. As with the bonding rolls 56, the laminating rolls 58 may be heated. Also, at least one of the rolls may be patterned to create a discrete bond pattern with a prescribed bond surface area for the resultant laminate 32. Generally, the maximum bond point surface area for a given area of surface on one side of the laminate 32 will not exceed about 50 percent of the total surface area. There are a number of discrete bond patterns which may be used. See, for example, Brock et al., U.S. Pat. No. 4,041,203 which is incorporated herein by reference in its entirety. Once the laminate 32 exits the laminating rolls 58, it may be wound up into a roll 60 for subsequent processing. Alternatively, the laminate 32 may continue in-line for further processing or conversion.

The process shown in FIG. 3 also may be used to create a three layer laminate 32 such as is shown in FIG. 2 of the drawings. The only modification to the previously described process is to feed a supply 62 of a second fibrous nonwoven web support layer 30 into the laminating rolls 58 on a side of the multilayer film 10 opposite that of the other fibrous nonwoven web support layer 30. As shown in FIG. 3, the supply of support layer 30 is in the form of a pre-formed roll 62. Alternatively, as with the other layers, the support layer 30 may be formed directly in-line. In either event, the second support layer 30 is fed into the laminating rolls 58 and is laminated to the multilayer film 10 in the same fashion as the other support layer 30.

Figure 4:
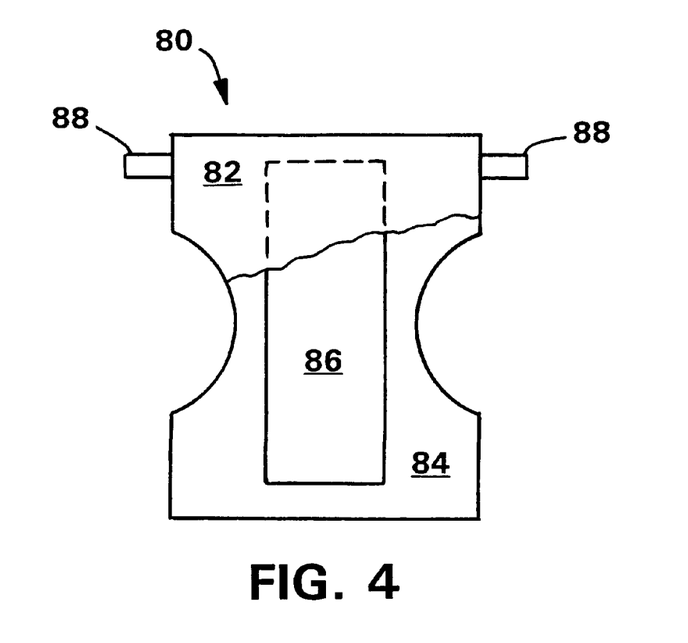
FIG. 4 is a partially cut away top plan view of an exemplary personal care absorbent article, in this case a diaper, which may utilize a multilayer film and multilayer film/nonwoven laminate according to the present invention.

As has been stated previously, the multilayer film 10 and the laminate 32 may be used in a wide variety of applications not the least of which includes personal care absorbent articles such as diapers, training pants, incontinence devices and feminine hygiene products such as sanitary napkins. An exemplary article 80, in this case a diaper, is shown in FIG. 4 of the drawings. Referring to FIG. 4, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type of fasteners.

The multilayer film 10 by itself or in other forms such as the multilayer film/support layer laminate 32 may be used to form various portions of the article including, but not limited to, the top sheet 82 and the back sheet 84. If the film is to be used as the liner 82, it will most likely have to be apertured or otherwise made to be liquid permeable. When using a multilayer film/nonwoven laminate 32 as the outercover 84, it is usually advantageous to place the nonwoven side facing out away from the user. In addition, in such embodiments it may be possible to utilize the nonwoven portion of the laminate 32 as the loop portion of the hook and loop combination.

Other uses for the multilayer film and multilayer film-support layer laminates according to the present invention include, but are not limited to, surgical drapes and gowns, wipers, barrier materials and articles of clothing or portions thereof including such items as workwear and lab coats.

TEST METHODS

The properties of the present invention were determined using a series of test procedures which are set forth below. These properties include film thicknesses, water vapor transmission rates and peel strengths.

Water Vapor Transmission Rate

The water vapor transmission rate (WVTR) for the sample materials was calculated in accordance with ASTM Standard E96-80. Circular samples measuring three inches in diameter were cut from each of the test materials and a control which was a piece of CELGARD® 2500 film from Hoechst Celanese Corporation of Sommerville, N.J. CELGARD®2500 film is a microporous polypropylene film. Three samples were prepared for each material. The test dish was a number 60-1 Vapometer pan distributed by Thwing-Albert Instrument Company of Philadelphia, Pa. One hundred milliliters of water was poured into each Vapometer pan and individual samples of the test materials and control material were placed across the open tops of the individual pans. Screw-on flanges were tightened to form a seal along the edges of each pan, leaving the associated test material or control material exposed to the ambient atmosphere over a 6.5 centimeter diameter circle having an exposed area of approximately 33.17 square centimeters. The pans were placed in a forced air oven at 100° F. (38° C). The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. After 24 hours, the pans were removed from the oven and weighed again. The preliminary test water vapor transmission rate values were calculated as follows:

Test WVTR=(grams weight loss over 24 hours)×315.5 g/m$^2$/24 hrs

The relative humidity within the oven was not specifically controlled.

Under predetermined set conditions of 100° F.(38° C.) and ambient relative humidity, the WVTR for the CELGARD® 2500 control has been defined to be 5000 grams per square meter for 24 hours. Accordingly, the control sample was run with each test and the preliminary test values were corrected to set conditions using the following equation:

WVTR=(Test WVTR/control WVTR)×5000 g/m$^2$/24 hrs.)(g/m$^2$/24 hrs)

Film/Film Laver Thicknesses

The overall thickness 28, first skin thickness 24, core thickness 22 and second skin thickness 26 can be measured in cross-section by Field Emission Scanning Electron Microscopy (FESEM). Each film sample was submersed in liquid nitrogen and cut on impact with a razor blade. The freshly cut cross-section was mounted to a specimen stub in an upright position using copper tape. The samples were observed using an Hitachi S-800 Field Emission Scanning Electron Microscope at 5 and 10 keV. Scanning electron photomicrographs were taken at 2000X _magnification to show the film structures for each sample. Three separate samples and corresponding pictures were prepared for each multilayer film. The 10.2 centimeter by 12.7 centimeter negatives were enlarged to 20.4 centimeter by 25.4 centimeter copies and the measurements were taken directly off these photographs. A reference 15 micron scale magnified at 2000X was superimposed on each photo. Five measurements for each of the layers was made on each of the three photos for each film sample thereby creating 15 datapoints or measurements for each thickness. Measurements were made for the first skin layer, the second skin layer and the core layer of each sample. The 15 measurements for each layer were combined and averaged to yield a thickness value in microns for each layer. The total thickness of the overall film was obtained by adding the average values for the core layer, first skin layer and second skin layer for each sample. The relative percentage of each skin layer was obtained by dividing the average thickness of the respective skin layer by the average overall thickness of the same sample and multiplying the result by 100 to yield percent.

180° T Peel Test

To test the bond strength between the film layer and the fibrous nonwoven comfort layer, a delamination or peel strength test was performed upon samples of the various materials. 10.2 centimeter (cm) by approximately 15.2 centimeter (cm) samples of the material were cut. To the film side of the samples there was applied a 10.2 cm by 15.2 cm piece of 3M 2308 masking tape. The sample were then rolled, tape side up, forward and backwards two times with a 22.2 kilogram roller weight. The samples were then manually delaminated at one of the short ends to produce edges which could be placed within the jaws of a Sintech®/2 Computer Integrated Testing System manufactured by MTS Systems Corporation of Eden Prairie, MN. The jaw gap was set at a span of 100 millimeters and enough of the material was left in the laminated state so that the jaws could travel 65 millimeters. The sample was positioned in the jaws so that the sample would start delaminating before the jaws had been expanded 10 millimeters. The crosshead speed was set at 300 millimeters per minute and the data were then recorded between the 10 millimeter start point and the 65 millimeter end point. The data recorded indicated the peel strength or load necessary in grams to separate the two layers and the standard index in grams with a maximum, minimum and mean value.

EXAMPLES

All the example films were three layer films with the two outer or skin layers in each example being the same. All films were cast films and the films in examples 1–5 were embossed prior to stretching to yield a matte finish on the films. In addition, the films in examples 1–5 were laminated to a 17 gram per square meter (gsm) polypropylene spunbond web made from approximately 2 denier fibers. The spunbond web was prebonded with a point bond pattern having an overall bond area of approximately 15 percent.

Example 1

In Example 1 the core layer was, on a weight percent basis based upon the total weight of the layer, 65 percent ECC Supercoat® calcium carbonate with a 1 micron average particle size and a 7 micron top cut. The calcium carbonate was obtained from ECCA Calcium Products, Inc. of Sylacauga, Al. which is a division of ECC International. The core layer also included 15 percent Exxon 9302 Random Copolymer Polypropylene (RCP) from the Exxon Chemical Company of Houston, Tex., 15 percent Himont KS059 Catalloy™ polymer from Himont U.S.A. of Wilmington, Del. and 5 percent Quantum NA206 Low Density Polyethylene (LDPE) from Quantum Chemical Corporation of New York, N.Y. The Himont Catalloy™ polymer is an olefinic thermoplastic elastomer or TPO multistep reactor product wherein an amorphous ethylene propylene random copolymer is molecularly dispersed in a predominately semicrystalline high polypropylene monomer/low ethylene monomer continuous matrix.

The two outer or skin layers on opposite sides of the core layer comprised 15 percent Himont KS057 Catalloym polymer from Himont U.S.A., 20 percent Ampacet™ 10115 antiblock and 65 percent Exxon XC-101 (28 percent EMA copolymer). Ampacet™ 10115 antiblock comprises 20 weight percent Superfloss™ diatomaceous earth let down in 79.75 percent Chevron 2207 EMA and 0.25 percent aluminum stearate. AmpaCet™ 10115 antiblock is available from Ampacet™ Corporation of Tarrytown, N.Y. Chevron 2207 EMA is available from the Chevron Chemical Corporation of San Ramon, Calif. and Exxon XC-101 is available from the Exxon Chemical Company of Houston, Tex.

The three layer film was extruded using cast extrusion equipment of the type described above. The exiting melt temperature for the skin layers was measured to be 196° C. and for the core was 223° C. The air gap (distance between the die and the nip chill roll) was 53 centimeters and the gauge of the resultant film was 38 micrometers (microns). The film was wound up on a roll and later sent through a Machine Direction Orienter (MDO) Model No. 7200 from the Marshall and Williams Company of Providence, R.I. The MDO unit was preheated to 77° C. and the film was stretched 4X while at a temperature of 77° C. By saying the film was stretched 4X it is meant that, for example, a 1 meter long film would be stretched to a resultant length of 4 meters. The final measured thickness of the film was 16.08 microns and the basis weight was 17 grams per square meter (gsm). Each of the two skin layers comprised approximately 2.7 percent of the overall film thickness. As a result, the core layer represented 94.6 percent of the overall thickness. Using the film thickness measuring method described above, the two skin layers each had a film thickness of 0.44 microns and the core layer had a thickness of 15.2 microns.

The resultant film was then thermally laminated to the above-described spunbond layer using a patterned bonding roll having a temperature of approximately 77° C. and a smooth anvil roll at a temperature of approximately 54° C. with a nip pressure of 4,218 kilograms per meter (kg/m) while at a line speed of 152 meters per minute with and overall bond area of 15 percent based upon the surface area of one side of the film. The laminate was passed through the bonder in such a fashion that the spunbond layer was adjacent the pattern roll and the film layer was adjacent the smooth anvil roll. The resultant laminate had a Water Vapor Transmission Rate (WVTR) measured as described above of 2570 grams per square meter per 24 hours (2570g/m$^2$/24hr or day). The laminate had a hydrohead of 70 centimeters and a peel strength of 48 grams.

Example 2

In Example 2 the core layer was, on a weight percent basis based upon the total weight of the layer, 65 percent ECC Supercoat® calcium carbonate, 15 percent Exxon 9302 Random Copolymer Polypropylene (RCP), 15 percent Himont KS059 Catalloy™ polymer and 5 percent Quantum NA206 Low Density Polyethylene (LDPE).

The two outer or skin layers on opposite sides of the core layer comprised 15 percent Ampacet™ 10115 antiblock (20 percent diatomaceous earth antiblock let down in a 24 percent copolymer ethylene methyl acrylate (EMA)) concentrate or masterbatch and 85 percent Himont KS057 Catalloy∩ polymer.

The three layer film was extruded using cast extrusion equipment of the type described above. The exiting melt temperature from the extruder for the skin layers was 188° C. and the melt temperature for the core layer was 223° C. The air gap (distance between the die heads and the forming nip) was 53 centimeters and the gauge of the resultant film was 35.5 microns. The film was wound up on a roll and later sent through the MDO unit which was preheated to 88° C. and the film was stretched 3x while at a temperature of 88° C. The final measured thickness of the film was 17.28 microns and the basis weight was 15 gsm. Each of the two skin layers comprised 2 percent of the overall film thickness. As a result, the core layer represented 96 percent of the overall thickness. Using the film thickness measuring method described above, the two skin layers each had a film thickness of 0.33 micrometers (microns) and the core layer had a thickness of 16.62 microns.

The resultant film was then thermally laminated to the above-described spunbond layer using a patterned bonding roll having a temperature of approximately 77° C. and a smooth anvil roll at a temperature of approximately 54° C. with a nip pressure of 4,218 kg/m while at a line speed of 152 meters per minute with and overall bond area of 15 to 18 percent based upon the surface area of one side of the film. The laminate was passed through the bonder in such a fashion that the spunbond layer was adjacent the pattern roll and the film layer was adjacent the anvil roll. The film had a Water Vapor Transmission Rate (WVTR) measured as described above of 925 grams per square meter per 24 hours and the laminate had a WVTR of 820g/m$^2$/24hr. The laminate had a hydrohead of 113 centimeters and a peel strength of 62 grams.

Example 3

In example 3 the core layer was, on a weight percent basis based upon the total weight of the layer, 63 percent ECC Supercoat® calcium carbonate, 19 percent Himont KS059 Catalloy™ polymer, 13 percent Shell 6D81 polypropylene from the Shell Chemical Company of Houston, Tex. and 5 percent Dow 4012 low density polyethylene (LDPE) from Dow Chemical U.S.A. of Midland, Mich.

The two outer or skin layers on opposite sides of the core layer comprised 30 percent Himont KS057 Catalloy™ polymer, 20 percent Techmer™ S110128E62 antiblock/EVA concentrate or masterbatch from Techmer™ PM of Rancho Dominguez, Calif., 20 percent Exxon 760.36 EVA and 30 percent Lotryl 29MA03 Ester-Modified EMA copolymer from Elf Atochem N.A. of Philadelphia, Pa.

The three layer film was extruded using cast extrusion equipment. The exiting temperature from the extruder for the skin layers was 188° C. and for the core was 209° C. The air gap (distance between the die heads and the forming roll) was 66 centimeters and the gauge of the resultant film was 38 microns. The film was wound up on a roll and later sent through the MDO unit which was preheated to 71° C. and the film was stretched 4× while at a temperature of 71° C. and subsequently annealed at a temperature of approximately 85° C.

The final gauge of the film was 16.98 microns and the basis weight was 17 gsm. Each of the two skin layers comprised 3.7 percent of the overall film thickness. As a result, the core layer represented 92.6 percent of the overall thickness. Using the film thickness measuring method described above, the two skin layers each had a film thickness of 0.6 microns and the core layer had a thickness of 15.77 microns.

The resultant film was then thermally laminated to the above-described spunbond layer using a patterned bonding roll having a temperature of approximately 110° C. and a smooth anvil roll at a temperature of approximately 32° C. with a nip pressure of 4570 kg/m inch while at a line speed of 61 meters per minute with and overall bond area of 15 to 18 percent based upon the per unit surface area of one side of the film. The laminate was passed through the bonder in such a fashion that the spunbond layer was adjacent the pattern roll and the film layer was adjacent the anvil roll. The film had a Water Vapor Transmission Rate (WVTR) measured as described above of 1301 grams per square meter per 24 hours (1301 g/m²/24hr) and the resultant laminate had a WVTR of 1184 g/m²/24hr. The laminate had a hydrohead of 110 centimeters and a peel strength of 161 grams.

Example 4

In Example 4 the core layer was, on a weight percent basis based upon the total weight of the layer, 63 percent ECC Supercoat® calcium carbonate, 19 percent Himont KS059 Catalloy™ polymer, 13 percent Shell 6D81 polypropylene and 5 percent Dow 4012 LDPE.

The two outer or skin layers on opposite sides of the core layer comprised 35 percent Himont KS057 Catalloy™ polymer, 20 percent Techmer™ 10128E62 antiblock/EVA concentrate/masterbatch and 45 percent Exxon 760.36 EVA.

The three layer film was extruded using cast extrusion equipment. The exiting temperature for the skin layers was 187° C. and for the core was 208° C. The air gap (distance between the die heads and the forming roll) was 66 centimeters and the gauge of the resultant film was 35.5 microns. The film was wound up on a roll and later sent through the MDO unit which was preheated to 71° C. and the film was stretched 4× while at a temperature of 71 ° C. and subsequently annealed at a temperature of approximately 85° C. The final measured thickness of the film was 15.96 microns and the basis weight was 15 gsm. Each of the two skin layers comprised 3.0 percent of the overall film thickness. As a result, the core layer represented 94.0 percent of the overall thickness. Using the film thickness measuring method described above, the two skin layers each had a film thickness of 0.48 microns and the core layer had a thickness of 15.0 microns.

The resultant film was then thermally laminated to the above-described spunbond layer using a patterned bonding roll having a temperature of approximately 110° C. and a smooth anvil roll at a temperature of approximately 66° C. with a nip pressure of 4570 kg/m while at a line speed of 61 meters per minute with and overall bond area of 15 to 18 percent based upon the per unit surface area of one side of the film. The laminate was passed through the bonder in such a fashion that the spunbond layer was adjacent the pattern roll and the film layer was adjacent the anvil roll. The resultant laminate had a WVTR of 1522 g/m²/24 hrs., a hydrohead of 89 centimeters and a peel strength of 148 grams.

Example 5

In Example 5 the core layer was, on a weight percent basis based upon the total weight of the layer, 65 percent ECC English China Supercoat® calcium carbonate, 15 percent Himont KS059 Catalloy polymer, 15 percent Exxon 9302 Random Copolymer Polypropylene (RCP) and 5 percent Dow 4012 LDPE.

The two outer or skin layers on opposite sides of the core layer comprised 35 percent Himont KS057 Catalloy™ polymer, 20 percent Techmer™ S110128E62 antiblock/EVA concentrate/masterbatch and 45 percent Exxon 760.36 EVA.

The three layer film was extruded using cast extrusion equipment. The exiting temperature for the skin layers was 175° C and for the core was 234° C. The air gap (distance between the die heads and the forming roll) was 33 centimeters and the gauge of the resultant film was 35.5 microns. The film was wound up on a roll and later sent through the MDO unit which was preheated to 77° C. and the film was stretched 4× while at a temperature of 77° C. and subsequently annealed at a temperature of approximately 75° C. The final measured thickness of the film was 16.92 microns and the basis weight was 15 gsm. Each of the two skin layers comprised 1.0 percent of the overall film thickness. As a result, the core layer represented 98.0 percent of the overall thickness. Using the film thickness measuring method described above, the two skin layers each had a film thickness of 1.75 microns and the core layer had a thickness of 16.57 microns.

The resultant film was then thermally laminated to the above-described spunbond layer using a patterned bonding roll having a temperature of approximately 73° C. and a smooth anvil roll at a temperature of approximately 51° C. with a nip pressure of 4218 kg/m while at a line speed of 152 meters per minute with and overall bond area of 15 to 18 percent based upon the per unit surface area of one side of the film. The laminate was passed through the bonder in such a fashion that the spunbond layer was adjacent the pattern roll and the film layer was adjacent the anvil roll. The resultant laminate had a WVTR of 1930 g/m²/24 hrs., a hydrohead of 66 centimeters and a peel strength of 116 grams.

As shown by the above examples of the present invention, very low thickness (less than 30 microns) multilayer films can be formed. In addition, such films can have very thin skin layers which can impart a wide variety of functionalities including making the film vapor permeable, liquid impermeable and adhesive in nature. Furthermore such films can be attached to other support layers such as nonwoven to form laminates.

Example 6

A multilayer film, having a core layer and opposed skin layers, having an overall basis weight of 59.1 gsm was formed by co-extrusion. The core film comprised 55% by weight Filmlink™ calcium carbonate filler coated with behenic acid (available from English China Clay); 40% by weight linear low density polyethylene (Dow NG3310, having a density of 0.918 g/cc); 5% by weight low density polyethylene (DOW 40121, having a density of 0.916 g/cc); and 2000 ppm anti-oxidant (CIBA B900 available from Ciba Specialty Products which is a 1:4 ratio of Irganox® 1076-a phenolic anti-oxidant and Irgafos™ 168-a phosphite stabilizer). Each of the skin layers comprised 50.4 % by weight ethylene-vinyl acetate copolymer (Exxon 768.36 which contains 28% vinyl acetate); 45.1% by weight polyolefin copolymer (Montell K5057P ethylene-propylene Catalloy™ polymer); and 4 % diatomeceous earth (Superfloss™ available from Celite Corp., a subsidiary or World Minerals of Lompoc, CA).

The multilayer film was heated over a series of pre-heat rolls at 200° F. The multilayer film was then stretched, in a single stretch operation, 4.0 times its original length using an MDO similar to that described herein above. The temperature of the slow roll was 195° F. and the temperature of the fast roll was 70° F. The stretched film was then run over a series of anneal rolls at 210° F. The annealed multilayer film then traveled to a thermal point bonder. The annealed multilayer film was allowed to retract prior to entering the bonder, and the retracted multilayer film had an average basis weight of 13.6 gsm. The bonding rolls of the thermal point bonder traveled at 88% of the anneal rolls. The patterned roll temperature was 235° F. and the anvil roll 215° F. The film was fed into the nip along with a 17.6 gsm (0.5 ounces per square yard) polypropylene spunbond fiber web. The resulting laminate had a WVTR of 4119 g/m²/day, hydrohead of 86 cm, an MD tensile of 9010 g and CD tensile of 3860 g and peel strength of 110 grams.

Example 7

A multilayer cast film having a core layer and opposed skin layers with an overall basis weight of 64 gsm was formed by co-extrusion. The core layer film consisted of 65% calcium carbonate filler coated with behenic acid (ECC Filmlink® 2029 available from English China Clay); 20.6% Union Carbide 6D82 random copolymer (ethylene-propylene copolymer, 5.5% by weight ethylene); 11.1% Montell KS570P Catalloy™ polymer (5 MFR); 3.3% Montell Catalloy™ KS359P polymer. The skin layers were comprised of 50% by weight of Fina 625 polystyrene and 50% Exxon Exxtracling$^\Psi$ XC101Ethylene methyl acrylate. The skin layers comprises of only 3.0% of the total thickness of the multilayer film.

The multilayer film was then stretched via two different methods and laminated to a spunbond. In the first method it was heated over a series of preheat rolls at 185° F. The film was then multi-zone stretched over two stretch zones to a total stretch length of 3.75 times its original length using an MDO similar to that described herein above. The temperatures of the slow speed roll was 185° F., the intermediate speed roll was at 185° F. and ambient temperature for the fast roll. The film was then run over another roll at ambient temperatures and finally annealed over two rolls at 210° F. The stretched, annealed film was allowed to retract to 80% of its stretched length before it was thermally point bonded to a 17 gsm (0.5 ounces per square yard) polypropylene spunbond fabric. The average basis weight of the laminate was 33 gsm. The patterned roll of the point bonder was 250° F. and the anvil roll was 190° F. The resulting laminate had a WVTR of 3283, a hydrohead of 67 cm and a peel strength of 40 grams.

In the second method, the multilayer film was preheated over a 200° F. roll and stretched in a single stretch operation to 4.0 times its original length. The slow roll was 185° F. and the fast roll was In the second method, the multilayer film was preheated over a 200° F. roll and stretched in a single stretch operation to 4.0 times its original length. The slow roll was 185° F. and the fast roll was at ambient temperature. The stretched film was then run over an annealing roll at 210° F. The stretched annealed film was then sprayed with molten Rextac® 2330 adhesive (an ethylene-propylene copolymer available from Rexene Products Co. of Dallas, Tex.) and immediately nipped to 17 gsm (0.5 osy) spunbond fabric. The molten adhesive was heated to 350° F. and sprayed through a die using pressurized air to approximately 3 gsm basis weight. The average total laminate basis weight was 37 gsm. The resulting laminate had a WVTR of 4200, a hydrohead of 214 cm, and peel strength of 939 grams.

Thus, the foregoing examples show multilayer films and laminates thereof wherein it has been possible to achieve a breathable microporous core film with opposed extremely thin skin layers (with little or no particulate loading) wherein the multilayer film and laminates thereof exhibit good bonding to the core film as well as the nonwoven thermoplastic fiber web. Moreover, despite the inclusion of skin layers with little or no particulate loading, the multilayer films of the present invention exhibit excellent WVTRs.

While the invention has been described in detail with respect to specific embodiments thereof, and particularly by the examples described herein, it will be apparent to those skilled in the art that various alterations, modifications and other changes may be made without departing from the spirit and scope of the present invention. It is therefore intended that all such alterations, modifications or other changes be encompassed by the claims.

What is claimed is:

1. A breathable multilayer film, comprising:
   a microporous breathable core layer, said core layer comprising an extrudable thermoplastic polymer and from about 40% to about 70% by weight filler and having a first exterior surface and a second exterior surface;
   a first breathable skin layer attached to said first exterior surface of said core layer, said first skin layer comprising an extrudable thermoplastic polymer composition comprising from zero to 70% by weight of a first polyolefin and from 30% to 70% of a polymer selected from the group consisting of ethylene vinyl acetate, ethylene ethyl acrylate, ethylene methyl acrylate, ethylene butyl acrylate, ethylene acrylic acid, ethylene vinyl alcohol, polyester, nylon, polystyrene, polyurethane, and olefinic thermoplastic elastomers, wherein said first skin layer has a thickness less than about 2 microns; and
   wherein said multilayer film has a total thickness less than 30 microns and an overall WVTR of at least 800 g/m$^2$/day and further wherein said multilayer film is liquid impermeable.

2. The multilayer film of claim 1 having a WVTR in excess of 2000 g/m$^2$/day.

3. The multilayer film of claim 1 wherein said first skin layer comprises from about 0.5 to about 10% by weight anti-block.

4. The multilayer film of claim 3 wherein said anti-block in said skin layer comprises diatomaceous earth.

5. The multilayer film of claim 1 having a second breathable skin layer attached to said core layer.

6. The multilayer film of claim 5 wherein each of said first and second skin layers comprises less than about 5% by weight anti-block.

7. The multilayer film of a claim 1 wherein said thermoplastic polymer of the first skin layer comprises a blend of polyolefin and an ethylene copolymer selected from the group of ethylene vinyl acetate and ethylene methyl acrylate.

8. The multilayer film of claim 1 having a WVTR in excess of 2000 g/m$^2$/day and wherein said first skin film comprises a blend of a polyolefin polymer and ethylene vinyl acetate.

9. The multilayer film of claim 8 wherein said first skin layer comprises a polyolefin polymer selected from the group of ethylene and propylene polymers.

10. A breathable laminate, comprising the multilayer film of claim 1, and a support fabric attached to said first skin layer.

11. The breathable laminate of claim 10 wherein said support fabric comprises a nonwoven fabric of thermoplastic fibers.

12. The breathable laminate of claim 11 wherein said support fabric is thermally laminated to said multilayer film at a plurality of discrete bond points.

13. A breathable laminate, comprising:
    the multilayer film of claim 5 further comprising a first support fabric attached to said first skin layer and a second support fabric attached to said second skin layer.

14. The breathable laminate of claim 13 wherein said support layer comprises a nonwoven fabric of thermoplastic polyolefin fibers.

15. The multilayer film of claim 8 wherein said core layer comprises a polyethylene and wherein said multilayer film has a thickness less than 20 microns.

16. The multilayer film of claim 1 wherein said core layer comprises a polyolefin and said skin layer comprises a blend of a polyolefin and ethylene methyl acrylate and further wherein said multilayer film has a total thickness less than about 20 microns and a WVTR of at least about 2000 g/m$^2$/day.

17. The multilayer film of claim 16 wherein said core layer comprises polyethylene.

18. The multilayer film of claim 1 wherein said core layer comprises a polyolefin and said skin layer comprises a blend of a polyolefin and ethylene ethyl acrylate and further wherein said multilayer film has a total thickness less than about 20 microns and a WVTR of at least about 2000 g/m$^2$/day.

19. The multilayer film of claim 18 wherein said core layer comprises a polyethylene.

20. The multilayer film of claim 1 wherein said skin layer comprises a polyolefin and from 40% to 60% by weight of a second polymer selected from the group consisting of ethylene vinyl acetate, ethylene ethyl acrylate, ethylene methyl acrylate, ethylene butyl acrylate, ethylene acrylic acid, ethylene vinyl alcohol, polyester, nylon, polystyrene, and polyurethane and further wherein said skin layer has a thickness less than 1 micron.

21. The multilayer film of claim 20 wherein said core layer comprises a polyolefin and wherein said multilayer film has a total thickness of less than about 20 microns and a WVTR of at least about 2000 g/m$^2$/24 hours.

22. The multilayer film of claim 21 further comprising a second breathable skin layer attached to said core layer and wherein said second skin layer has a thickness less than 1 micron.

23. A breathable laminate comprising the multilayer film of claim 21 and a support fabric attached to said skin layer.

24. The breathable laminate of claim 23 wherein said support fabric comprises a nonwoven fabric of thermoplastic fibers.

25. The breathable laminate of claim 24 wherein said support fabric is thermally laminated to said multilayer film at a plurality of discrete bond points.

26. A breathable laminate comprising the multilayer film of claim 22 wherein said first and second skin layers comprise a blend of a polyolefin and a polymer selected from the group consisting of ethylene vinyl acetate, ethylene ethyl acrylate, ethylene methyl acrylate, ethylene butyl acrylate, ethylene acrylic acid and olefinic thermoplastic elastomers.

27. A breathable laminate, comprising the multilayer film of claim 26, and a nonwoven fabric of thermoplastic fibers.

28. The breathable laminate of claim 27 wherein said nonwoven fabric is thermally laminated to said multilayer film at a plurality of discrete bond points.

29. The multilayer film of claim 5 wherein said core layer comprises a polyolefin and wherein said multilayer film has a total thickness less than about 20 microns.

30. The multilayer film of claim 29 wherein said first and second skin layers each have a thickness less than about 0.5 microns and wherein said multilayer film has a WVTR of at least about 2000 g/m$^2$/24 hours.

31. The multilayer film of claim 1 wherein said skin layer comprises 30% to 70% polystyrene and from 30% to 70% of a second polymer selected from the group consisting of ethylene vinyl acetate and ethylene methyl acetate.

32. The multilayer film of claim 31 wherein said core layer comprises a polyolefin and wherein skin layer has a thickness less than about 0.5 microns and further wherein said multilayer film has a total thickness less than about 20 microns and a WVTR of at least about 2000 g/m$^2$/24 hours.

* * * * *